US010047342B2

(12) United States Patent
Eibl et al.

(10) Patent No.: US 10,047,342 B2
(45) Date of Patent: Aug. 14, 2018

(54) ELUTRIATION CHAMBER FOR AN ELUTRIATOR SYSTEM

(71) Applicant: BIO-PRODUCTS & BIO-ENGINEERING AG, Vienna (AT)

(72) Inventors: Johann Eibl, Vienna (AT); Johann Graus, Vienna (AT); Christoph Mader, Korneuburg (AT)

(73) Assignee: BIO-PRODUCTS & BIO-ENGINEERING AG, Vienna (AT)

( * ) Notice: Subject to any disclaimer, the term of this patent is extended or adjusted under 35 U.S.C. 154(b) by 249 days.

(21) Appl. No.: 14/399,406

(22) PCT Filed: May 13, 2013

(86) PCT No.: PCT/EP2013/059761
§ 371 (c)(1),
(2) Date: Nov. 6, 2014

(87) PCT Pub. No.: WO2013/167747
PCT Pub. Date: Nov. 14, 2013

(65) Prior Publication Data

US 2015/0111295 A1 Apr. 23, 2015

(30) Foreign Application Priority Data

May 11, 2012 (AT) .............................. A 50173/2012

(51) Int. Cl.
*C12N 5/00* (2006.01)
*A61M 1/36* (2006.01)
(Continued)

(52) U.S. Cl.
CPC ......... *C12N 5/0644* (2013.01); *A61M 1/3692* (2014.02); *A61M 1/3693* (2013.01);
(Continued)

(58) Field of Classification Search
CPC ............... A61M 1/3693; B01D 21/262; B01D 2221/10; B04B 5/0442; B04B 2005/0471; C12N 5/0644; C12M 47/04
(Continued)

(56) References Cited

U.S. PATENT DOCUMENTS 4,322,298 A * 3/1982 Persidsky ............. B04B 5/0428 210/516
4,939,087 A 7/1990 Van Wie et al.
(Continued)

FOREIGN PATENT DOCUMENTS

DE 2701976 7/1978
EP 0824380 2/1998
(Continued)

OTHER PUBLICATIONS

International Preliminary Report on Patentability dated Nov. 11, 2014 (PCT Application Serial No. PCT/EP2013/059761).

*Primary Examiner* — Walter D. Griffin
*Assistant Examiner* — Shuyi S. Liu
(74) *Attorney, Agent, or Firm* — Workman Nydegger

(57) ABSTRACT

The invention relates to an elutriation chamber for an elutriator system for washing and/or isolating cells, in particular thrombocytes, which elutriation chamber comprises a feed line (1) for an aqueous medium containing the cells to be washed and/or to be isolated in suspended form, and a discharge line (2) for the washed and/or isolated cells, wherein the chamber (5) is rotationally symmetrical to the axis (a), characterized in that the ratio of the area of the section through the lumen of the chamber (5) perpendicular to the axis (a) at the widest point (5*a*-5*b*) to the area of the section (1*a*) through the feed line (1) is in the range of 1,000 to 250,000.

Figure 1:
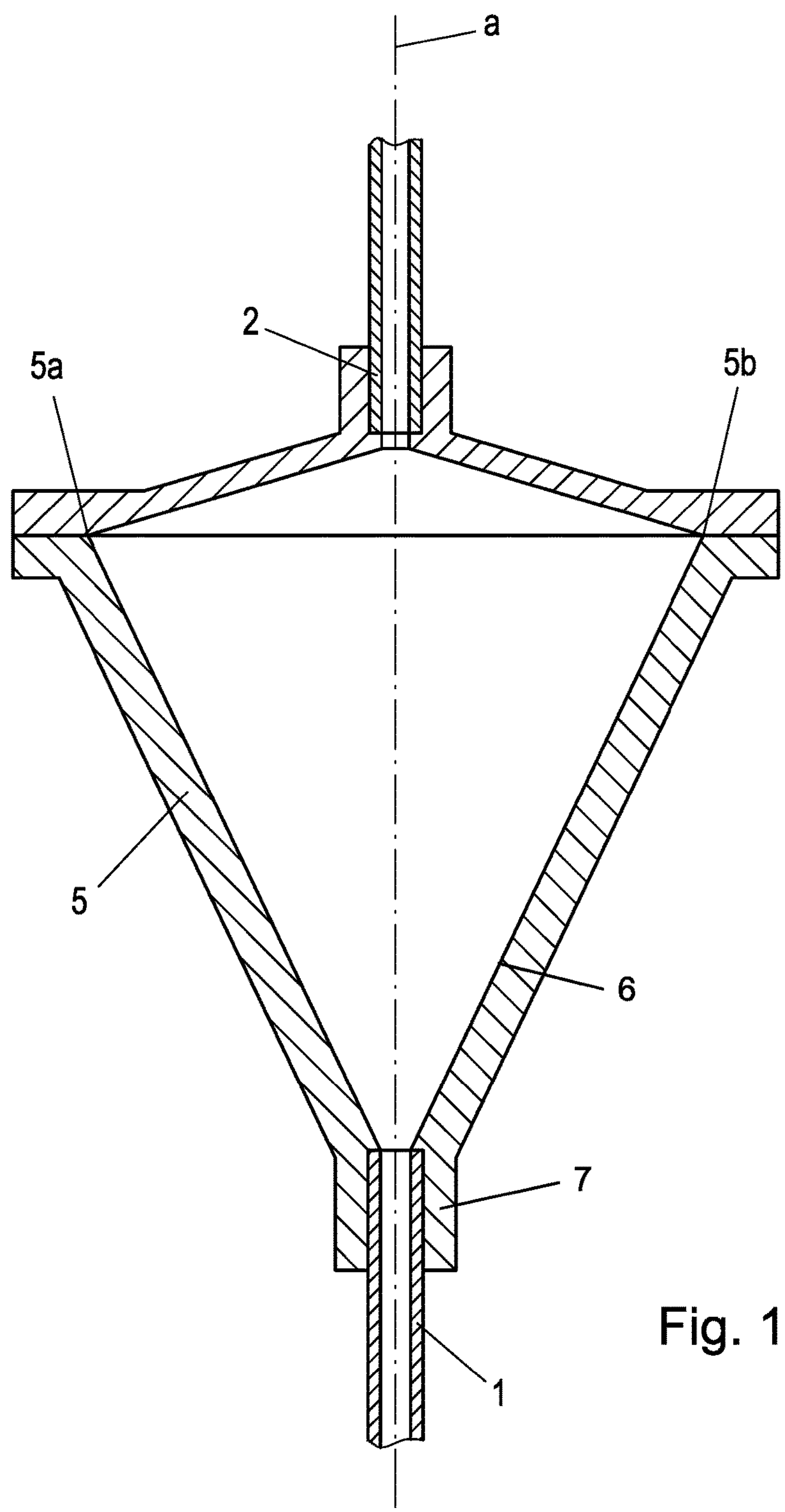

10 Claims, 4 Drawing Sheets a
2
5a
5b
5
6
7
1

(51) Int. Cl.
*B01D 21/26* (2006.01)
*B04B 5/04* (2006.01)
*C12M 1/00* (2006.01)
*C12N 5/078* (2010.01)

(52) U.S. Cl.
CPC ......... *A61M 1/3696* (2014.02); *B01D 21/262* (2013.01); *B04B 5/0442* (2013.01); *C12M 47/04* (2013.01); *A61M 2202/0427* (2013.01); *B01D 2221/10* (2013.01); *B04B 2005/0471* (2013.01)

(58) Field of Classification Search
USPC .................................... 435/325, 309; 494/22
See application file for complete search history.

(56) References Cited

U.S. PATENT DOCUMENTS

| | | | |
|---|---|---|---|
| 5,674,173 A | 10/1997 | Hlavinka et al. | |
| 6,309,606 B1 * | 10/2001 | Sitar ..................... | B01L 3/5021 422/533 |
| 2006/0147895 A1 * | 7/2006 | Purdum ................... | A01N 1/02 435/2 |
| 2008/0318756 A1 | 12/2008 | Langley et al. | |
| 2011/0021333 A1 * | 1/2011 | Sweat .................. | G01N 15/042 494/8 |

FOREIGN PATENT DOCUMENTS

| | | | |
|---|---|---|---|
| EP | 02169380 | 3/2010 | |
| EP | 2169380 A2 * | 3/2010 | ........... G01N 15/042 |
| WO | WO9923471 | 5/1994 | |
| WO | WO 9923471 A1 * | 5/1999 | ............ B01L 3/5021 |

* cited by examiner

ELUTRIATION CHAMBER FOR AN ELUTRIATOR SYSTEM

The invention relates to an elutriation chamber for an elutriator system for washing and/or isolating cells, in particular thrombocytes.

INTRODUCTION

The production of human blood cells from suitable blood donors by using centrifuges has so far been aimed at separating blood, after it has left the donor, into blood components in a tube system and an appropriate centrifuge in a process which is as continuous as possible, isolating the desired component and returning all other components directly into the donor. That process is designated apheresis. Through plasmapheresis it has become possible to obtain large amounts of blood plasma for the production of drugs for treating serious diseases while protecting the donor to the greatest possible extent. In analogy to plasmapheresis, it has also been possible to obtain the required amounts of thrombocyte-rich plasma by thrombapheresis.

For the production of plasma and thrombocytes, the construction of specific continuous centrifuges was necessary which were suitable also for the extraction and purification of other human cells, in particular bone marrow cells.

Problem

In comparison to most other blood cells, thrombocytes are small cells which do not possess a cell nucleus. In the circulating blood, on average, 200,000 to 300,000 thrombocytes are present per μl. In cases of thrombocytopenia, the number of thrombocytes may initially drop to 40,000 cells per μl without the occurrence of any noticeable symptoms. If the number of the thromboyctes continues to decrease, in particular to a range of 1,000 to 10,000 thrombocytes per μl, bleedings may occur which are more or less severe and are hard to stop. Such bleedings may lead to hemorrhage to death.

Thrombocytopenia may occur due to various primary diseases or can be caused by drugs, in particular by cytostatics. Initially, the treatment of thrombocytopenia could be performed successfully by transfusing fresh stored blood. The drawback of said treatment was that patients can be provided with blood transfusions only to a limited extent and, hence, the required number of thrombocytes in the circulating blood is not achieved in the long run.

After it had been accomplished to successfully obtain platelet-rich plasma from blood bottles directly after blood taking, the possibility of a more frequent application and of an appropriate treatment even of severe thrombocytopenia arose. The situation was further improved after it had become possible via thrombapheresis to obtain thrombocyte-rich plasma instead of whole blood. The frequency of donations of individual blood donors could thereby be increased.

Patients suffering from severe thrombocytopenia, which often receive infusions of thrombocyte-rich plasma, may very frequently be afflicted with serious side effects. Part of those side effects may be attributed to the infusion of thrombocytes, another part to the blood plasma still contained in the thrombocyte-rich plasma. In order to remove said plasma, it has been attempted to pelletize the platelets by centrifugation, to remove the plasma-containing supernatant and to re-suspend the platelet pellet again in suitable buffer solutions. This procedure, however, has the disadvantage that pelletized platelets can be resuspended well only with difficulty so that platelet aggregates will form which can no longer be dissolved into individual platelets. Due to the aggregation of platelets also a more or less strong activation of the may occur and thus also an increase in the risk of thrombus formation. Based on those circumstances, it appears to be desirable to separate plasma and microbial contaminants, which may be found in the plasma, from the platelets by an improved washing process. Furthermore, such a separation process should prevent any activation of the platelets to the greatest possible extent, should be feasible in an entirely aseptic way and also should remove other cells, in particular white blood cells which are still present.

Prior Art

A number of devices and equipments are already commercially available for scientific purposes and for the preparation of cell suspensions for medical applications. Both, autologous and homologous cell preparations from blood and tissues may therewith be obtained. Such devices and equipments serve for the extraction and purification, respectively, of cells in continuous centrifuges.

In the production of plasma by plasmapheresis, the plasma obtained still may be contaminated with different blood cells. However, such impurities are no obstacle to the application for the production of drugs. However, the platelet-rich plasma preparations obtained by thrombapheresis display several drawbacks, notably the contamination with other blood cells. Also, the plasma contained in the platelet-rich plasma may entail disadvantages when applied to humans.

The removal of white blood cells, which are located in the platelet-rich plasma by filtration is not a satisfactory solution. The leukocytes are indeed adsorbed on the filter and are thereby removed, but they are destroyed after their adsorption. Thus, the cell content of the leukocytes re-enters the filtrate and hence the thrombocyte concentrate.

The removal of plasma from the platelet-rich plasma by centrifugation should be avoided as far as possible. By sedimentation of the thrombocytes, the supernatant plasma can indeed be mostly removed, but the sedimented thrombocytes form a pellet, which is hard to resuspend completely. In addition, the major part of the resuspended thrombocytes are aggregated and partly also activated. In an intravenous application of such thrombocyte suspensions, this causes an increased risk of thrombosis for the recipient.

For the separation and isolation of those cells, the so-called elutriation is known which is based on the principle of counterflow centrifugation (e.g., U.S. Pat. No. 5,674,173, and EP 0 824 380 B1). Two forces acting against each other are thereby relevant: on the one hand, the outwardly directed centrifugal force which is determined by the rotational speed of the elutriator rotor and, on the other hand, the centripetal force which is determined by the flow speed of the medium in the direction of the axis of rotation by means of a pump. If both forces are in equilibrium, particles of a certain size and density can be concentrated in the elutriation chamber, while the remaining ones are washed out.

Solution to the Problem

In order to separate thrombocytes from a platelet-rich plasma, in a continuous centrifuge, the influx to the elutriation chamber is equipped with an appropriately dimensioned tube. The flow speed in said tube at a given number of revolutions of the centrifuge is kept so high during the overall process that no platelet-rich sediment will form in the feed tube. In this way, an unnecessary loss of thrombocytes is avoided and leukocytes can be removed.

The inlet opening into the elutriation chamber is preferably kept so small that the inlet speed of the platelet-rich plasma will be about 5 m/s. By that it is possible to suppress the Coriolis effect, which guides the thrombocytes toward the funnel wall of the elutriation chamber and along the funnel wall directly into the drain of the elutriation chamber, whereby the main part of the thrombocytes will be lost.

The thrombocyte-rich plasma introduced into the elutriation chamber at a high flow speed results very quickly to the formation of a platelet-rich central layer in the elutriation chamber. After the entire platelet-rich plasma has been introduced, the thrombocytes can be washed very well without significant losses by a uniform supply of suitable buffer solutions.

By applying a second inlet opening in the upper funnel of the elutriation chamber, the thrombocyte layer may be obtained without any overflow of liquid from the supplying tube at the entrance opening of the elutriation chamber.

Thereby, the individual elutriation process can also be performed aseptically.

The elutriation chamber according to the invention for an elutriator system for washing and/or isolating cells, in particular thrombocytes, which elutriation chamber comprises a feed line (1) for an aqueous medium containing the cells to be washed and/or to be isolated in suspended form, and a discharge line (2) for the washed and/or isolated cells, wherein the chamber (5) preferably being rotationally symmetrical to the axis (a), is characterized in that the ratio of the area of the section through the lumen of the chamber (5) perpendicular to the axis (a) at the widest point (5*a*-5*b*) to the area of the section (1*a*) through the feed line (1) is in the range of 1,000 to 250,000.

A further elutriation chamber according to the invention is characterized in that it comprises a further feed line (3) for a gaseous or liquid medium.

A preferred embodiment of an elutriation chamber according to the invention is characterized in that the ratio of the area of the section through the lumen of the chamber (5) perpendicular to the axis (a) at the widest point (5*a*-5*b*) to the area of the section (1*a*) through the feed line (1) is in the range of 1,000 to 250,000 and that it comprises a further feed line (3) for a gaseous or liquid medium.

A further elutriation chamber according to the invention for an elutriator system is finally characterized in that, between the feed line (1) and the chamber (5), a narrowing (4) is provided which preferably is designed conically in such a way that the ratio between the area of the section through the lumen of the chamber (5) perpendicular to the axis (a) at the widest point (5*a*-5*b*) to the area of the section through the narrowing (4) is in the range of 1,000 to 250,000. Said narrowing acts as a nozzle and accelerates the jet of liquid entering the chamber.

Further preferred embodiments of the elutriation chamber according to the invention are indicated in the appended claims.

Finally, the invention also relates to a method of removing unwanted contaminants such as microparticles, microbial pathogens, plasma proteins, photodynamic and other virus-inactivating agents from thrombocytes, by using an elutriation chamber according to the invention, with the proviso that the thrombocytes are not pelletized in said method.

Preferred embodiments are described in further detail on the basis of the accompanying drawing.

FIG. 1 shows an elutriation chamber (having a lumen 6 and a chamber entrance 7) contained in a commercially available elutriator system.

Said chamber is anchored on the centrifuge rotor with its axis of symmetry along the radius so that the fluid supply (1) is located close to the periphery of the rotor and, correspondingly, the fluid discharge (2) is located close to the axis. During the operation of the centrifuge, the respective fluid streams can now be introduced and discharged, respectively, via the rotor axis and generate in the chamber the stream directed against the centrifugal acceleration. Due to expansion of the chamber cross-section in the centripetal direction and the continuously decreasing flow speed associated therewith, an equilibrium between the centrifugal and resisting forces acting on a particle may be achieved within certain limits. By that, particles of an appropriate range of sedimentation speeds in the system are held in suspense, while the remaining portions of the fluid are washed out continuously.

The constructive connection of the supply and the discharge of the elutriation chamber via the axis of rotation necessitates a feed channel which, coming from the centre of the rotor, must be deflected directly in front of the separation chamber at the periphery of the rotor into a direction extending radially to the rotor axis. Since thereby the wall of the channel must extend in one point normally to the particle motion resulting from the sedimentation and flow speeds, this area is prone to massive formation of pellets, especially in case of particles which tend to agglutinate, such as, e.g., thrombocytes, which operates detrimental to the intended application.

Figure 2:
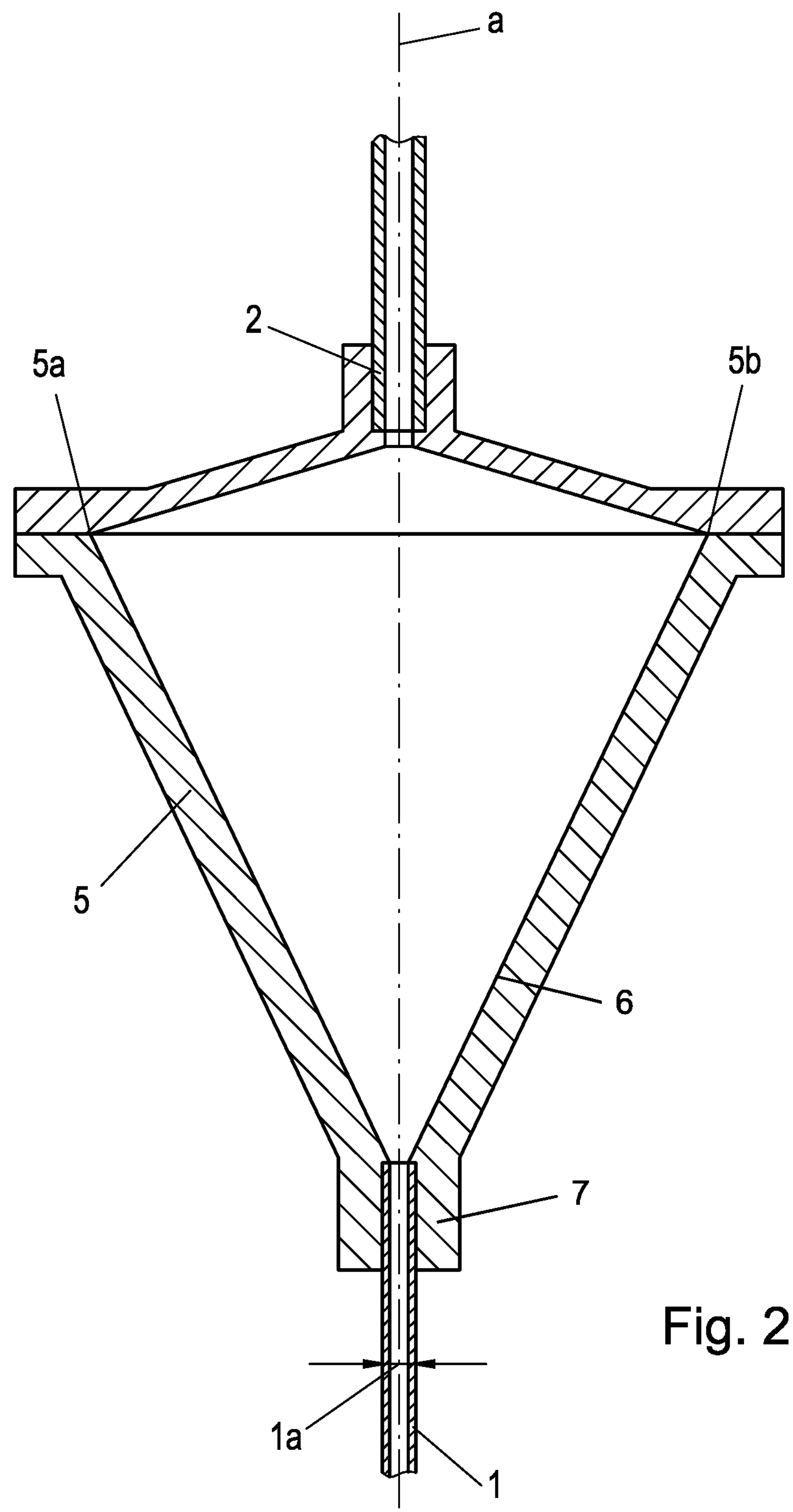

FIG. 2 shows an elutriation chamber (having a lumen 6 and a chamber entrance 7) according to the invention, wherein the feed line (1) has a cross-section which is so narrow that, with the applied flow rate, a transmission rate of more than 2 cm/s, preferably >10 cm/s (7 to 16 cm/s), is achieved. By increasing the flow rate via a reduced conduit cross-section, the pellet formation in the area of the deflection of the supplied fluid stream into the centripetal direction is counteracted directly in front of the separation chamber. It is thereby crucial that the ratio of the area of the section through the lumen of the chamber (5) perpendicular to the axis (a) at the widest point (5*a*-5*b*) to the area of the section (1*a*) through the feed line (1) is in the range of 1,000 to 250,000.

Figure 3:
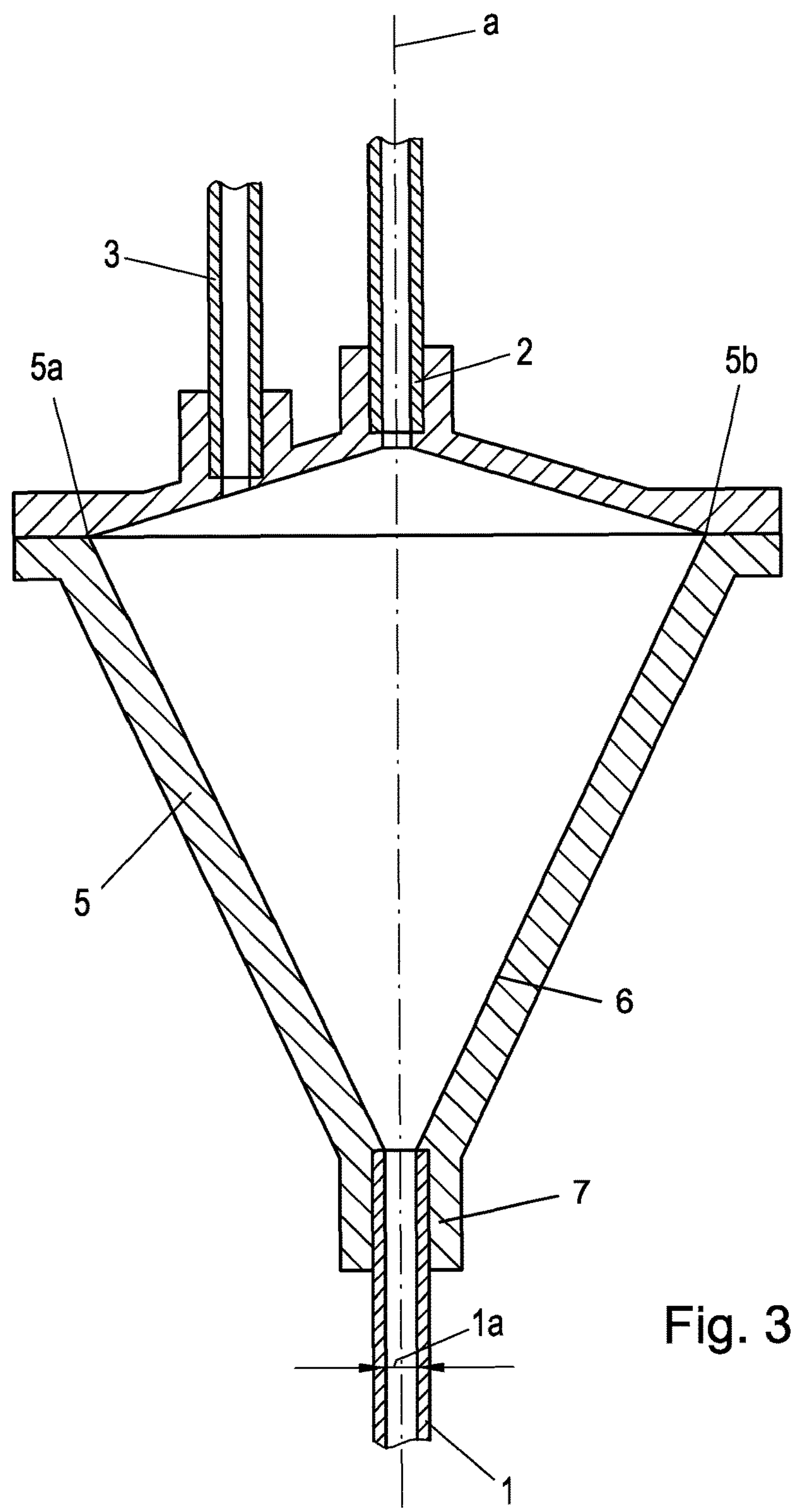

FIG. 3 shows a further elutriation chamber (having a lumen 6 and a chamber entrance 7) according to the invention comprising a further direct inlet (3) which is independent of the normal feed line (1) which serves for loading and the counterflow. At the end of the process, said inlet serves as a clean supply for extracting the content of the chamber without any material that has sedimented in the normal supply being dragged into the chamber and mixed with its contents.

Figure 4:
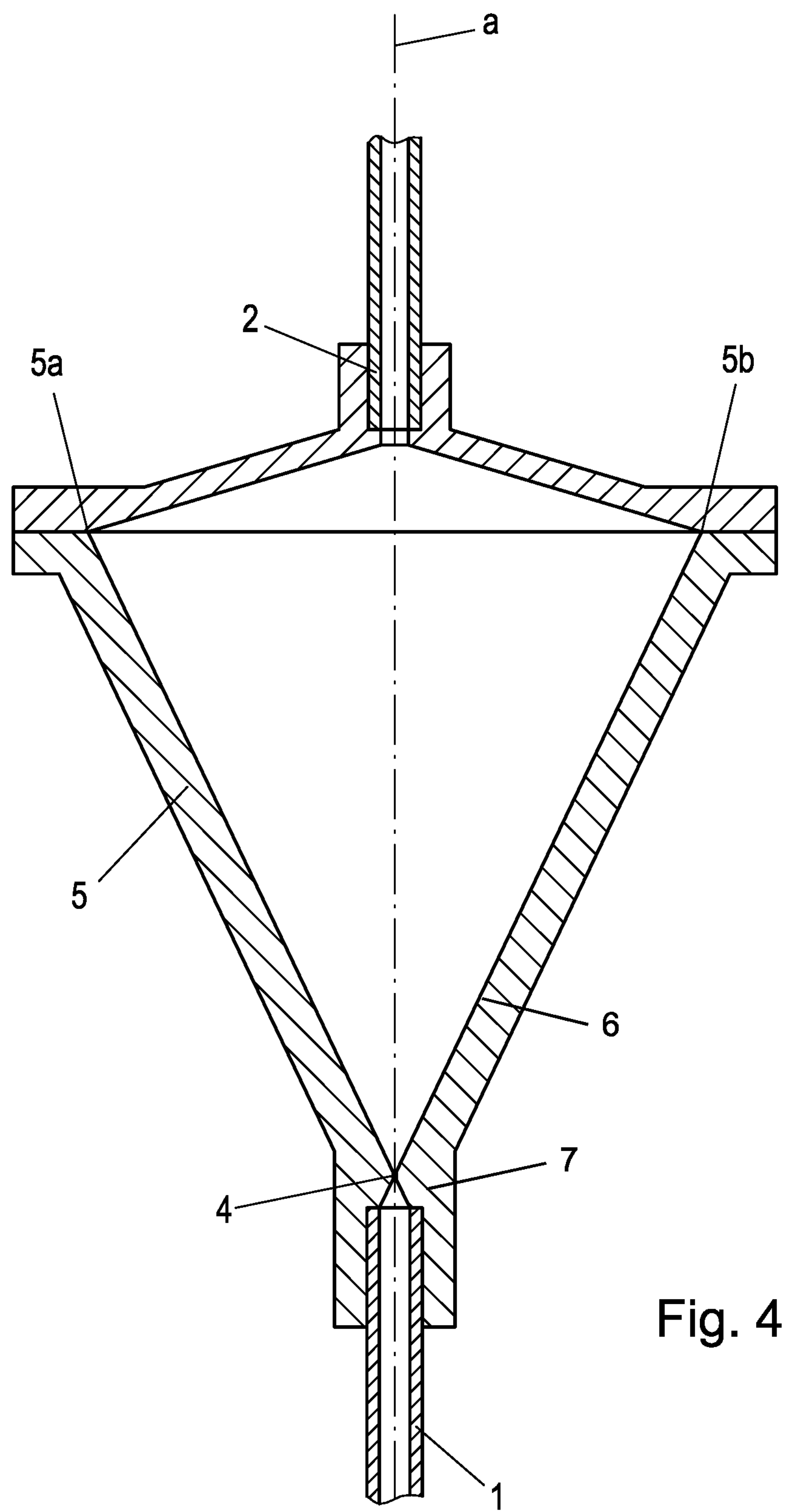

FIG. 4 shows an additional elutriation chamber (having a lumen 6 and a chamber entrance 7) according to the invention, wherein a strong narrowing of the inflow cross-section (4) is provided in the feed line (1). Through a simple interruption of the influx after elutriation has taken place, this enables an almost complete and effective separation of the chamber lumen from the normal supply line and thus prevents carry-over of material sedimented therein by diffusion or minor pressure fluctuations. During elutriation, the narrowing of the supply ensures a reduction in the extent of the creeping backflow from the chamber into the supply line along the wall facing away from the direction of rotation, which is caused by the Coriolis force. Furthermore, a dispersion of the inflowing fluid across the chamber cross-section is caused by the jet entering at a high speed and the turbulence associated therewith in the inflow area, which, on the one hand, contributes to an effective washing and, on the other hand, counteracts the formation of a channel flow along the chamber wall located in the direction of rotation as a result of the Coriolis force.

A preferred embodiment of the elutriation chamber according to the invention is described in the following example and consists in a combination of all three variants illustrated in FIGS. 2, 3 and 4.

EXAMPLE

The elutriation chamber manufactured from a transparent synthetic material is essentially composed of two straight hollow cones connected at their bases so that a chamber in the shape of a double cone emerges. It has its widest point (5*a*-5*b*) with an inner diameter of 50 mm on the common circular section, from where the two hollow cones extend 51 mm and 8 mm, respectively, toward their tips in each case in opposite directions.

This base body is oriented with its axis of symmetry (a) in the centrifuge rotor along the radius in such a way that the tip of the low cone points in the direction of the rotor axis and, accordingly, that of the high cone points toward the periphery of the rotor. For the supply (1) during normal operation, a narrowing (4) to a diameter of 0.3 mm is provided at the tip of the high cone, which tip is located peripherally to the rotor axis, the narrowing expanding conically toward the outside to the inner diameter of the attached supply tube of 1.2 mm. The ratio of the area of the section through the lumen of the chamber (5) perpendicular to the axis (a) at the widest point (5*a*-5*b*) perpendicular to the axis (a) to the area of the section (1*a*) through the feed line (1) thus amounts to 1736 (1962 $mm^2$/1.13 $mm^2$). The ratio of the cross-sectional areas increases to 27778 (1962 $mm^2$/0.071 $mm^2$), if a narrowing to 0.3 mm on average is provided.

At the cone tip which is situated opposite thereto and in close proximity to the rotor axis, the outlet port having a diameter of 2.9 mm is located, which opens into the discharge tube having the same inner diameter. For emptying out the contents of the chamber independently of the normal supply, the generated surface of the flat hollow cone additionally includes 14 mm acentrically of the axis of symmetry, a further inlet port (3) which has a diameter of 2.9 mm and is connected to the corresponding supply tube.

That centrifuge insert is installed on the rotor of a commercially available elutriation system which provides both peristaltic pumps for ensuring the required liquid streams and a connection to the corresponding supply and discharge lines of the rotating chamber.

The two supply lines are brought together outside of the rotor via a three-way cock and subsequently are connected to a multiple-way cock for supplying the respective liquid via a drip chamber and a pump. The discharge line leaving the rotor leads to two mutually switchable containers, on the one hand, for collecting the processed fraction and, on the other hand, for accommodating all the remaining liquids.

At the start of the process, the chamber and the entire piping is filled with a suitable solution, the centrifuge is brought to a number of revolutions of 2600 $min^{-1}$, and a continuous stream of 5 ml/min is established across the chamber supply which, for normal operation, is located at the periphery of the rotor, wherein the second supply line intended for evacuation is closed at the three-way cock.

Upon establishment of a steady flow through the system, the chamber is loaded through a continuous supply of the entire platelet-rich plasma, which is diluted in an appropriate buffer solution. Subsequently, the flow continues to be maintained with a suitable washing solution. If the required extent of washing has been achieved, the flow and the centrifuge are stopped at the same time, and an interconnection between only two chamber supplies is established via the three-way cock. After the elutriation chamber has been removed from the anchorage of the rotor and has been oriented with the discharge opening downward, as well as after the switching of the discharge line, the contents of the chamber are now pressed with air into the collecting vessel for the processed fraction exclusively via the second, additional supply line.

The elutriation chamber according to the invention permits the extraction of cells and cell components, whereby the supplying tube being dimensioned such that no thrombocyte-rich pellet can be formed during the elutriation process.

Furthermore, the elutriation chamber according to the invention allows high inflow speeds of the cell suspension or the suspension of cell fragments, which is to be cleaned, ranging between 1 and 10 m/sec, preferably of 5 m/sec.

If two discharge openings are provided in the upper funnel part of the elutriation chamber, that embodiment enables the extraction of elutriated cells or cell components without contamination with particles which are still present in the feed tube to the elutriation chamber.

In addition, the narrowing of the liquid entry into the elutriation chamber allows to achieve a high flow speed of the cell suspensions or the suspensions of cell components and to minimize the consequences of the Coriolis effect.

The invention claimed is:

1. An elutriation device for an elutriator system, the elutriation device having a chamber for washing and/or isolating cells, in particular thrombocytes, which elutriation device comprises:

a feed line for an aqueous medium containing the cells to be washed and/or to be isolated in suspended form, a chamber lumen, a discharge line for the washed and/or isolated cells, and an axis extending from the feed line to the discharge line, wherein a ratio of an area of a section through the chamber lumen perpendicular to the axis at a widest point to the area of a section through the feed line is in a range of 1,000 to 250,000.

2. An elutriation device according to claim 1, further comprising a further feed line for a gaseous or liquid medium.

3. An elutriation device for an elutriator system, the elutriation device having a chamber for washing and/or isolating cells, in particular thrombocytes, which elutriation device comprises:

a chamber entrance, a feed line coupled to the chamber at the chamber entrance, the feed line having a circular cross-section for passing an aqueous medium containing the cells to be washed and/or to be isolated in suspended form through the narrowing of the chamber entrance and into the chamber, a lumen of the chamber, a discharge line for the washed and/or isolated cells, and an axis extending from the feed line to the discharge line, wherein, in the feed line at the chamber entrance, a narrowing is provided in such a way that a ratio between an area of a section through the lumen of the chamber perpendicular to the axis at a widest point to an area of a section through the narrowing is in a range of 1,000 to 250,000.

4. An elutriation device according to claim 1, further comprising a chamber entrance provided with a narrowing, the feed line being coupled to the chamber at the chamber entrance such that the aqueous medium containing the cells is passed through the narrowing of the chamber entrance and into the chamber.

5. An elutriation device according to claim 3, further comprising a further feed line for a gaseous or liquid medium.

6. An elutriation device according to claim 1, wherein the chamber is rotationally symmetrical about the axis.

7. An elutriation device according to claim 1, wherein the feed line has a circular cross-section.

8. An elutriation device according to claim 3, wherein the narrowing at the chamber entrance is conical.

9. An elutriation device according to claim 4, wherein the narrowing at the chamber entrance is conical.

10. An elutriation device according to claim 3, wherein the chamber is rotationally symmetrical about the axis.

* * * * *